United States Patent
Szymanik

(10) Patent No.: US 7,021,315 B1
(45) Date of Patent: Apr. 4, 2006

(54) DEVICE FOR ORAL CAVITY PROCEDURE INTERVENTION

(76) Inventor: John H. Szymanik, 3189 Aldan Rd., Plymouth Meeting, PA (US) 19462

( * ) Notice: Subject to any disclaimer, the term of this patent is extended or adjusted under 35 U.S.C. 154(b) by 161 days.

(21) Appl. No.: 10/409,412

(22) Filed: Apr. 8, 2003

Related U.S. Application Data

(60) Provisional application No. 60/370,950, filed on Apr. 8, 2002.

(51) Int. Cl.
*A61G 15/00* (2006.01)

(52) U.S. Cl. ...................................................... 128/845

(58) Field of Classification Search .................. 128/845
See application file for complete search history.

(56) References Cited

U.S. PATENT DOCUMENTS

| | | | | | |
|---|---|---|---|---|---|
| 3,596,795 | A | * | 8/1971 | D'Ercoli | 206/514 |
| 5,987,676 | A | * | 11/1999 | Littleford et al. | 5/636 |
| 6,182,314 | B1 | * | 2/2001 | Frydman | 5/648 |

OTHER PUBLICATIONS

Terry Abrams, "Tube 'Em in the Streets," *Jems,* Apr. 1995, pp. 30-40.

* cited by examiner

*Primary Examiner*—Henry Bennett
*Assistant Examiner*—Camtu Nguyen
(74) *Attorney, Agent, or Firm*—Drinker Biddle & Reath LLP; Daniel A. Monaco

(57) ABSTRACT

An adjustable mechanical device for providing necessary leverage to a healthcare provider performing an intubation on a patient, and more particularly, a portable medical device for use by a paramedic or PHRN in facilitating an intubation on a patient.

18 Claims, 8 Drawing Sheets

DEVICE FOR ORAL CAVITY PROCEDURE INTERVENTION

FIELD OF THE INVENTION

The present invention relates generally to the field of emergency medicine and to a device for oral cavity or cephalic region procedure intervention in a mammal and, more particularly, to a device providing a user with a mechanical leverage to facilitate oral cavity or cephalic procedure intervention in a mammal.

BACKGROUND OF THE INVENTION

Intubation is a procedure where a healthcare provider inserts a breathing tube through a patient's mouth into the trachea to ensure a patent airway for the delivery of anesthetic gases or oxygen or both. Patients in a hospital setting may require such intubation as a result of obstructed airway, respiratory distress, or respiratory arrest. It also may be required in an operating room when a patient is under general anesthesia. Outside the hospital, intubation may be required in various emergency settings, such as a motor vehicle accident, a building collapse, or any other situation where a person is experiencing obstructed airway, respiratory distress, or respiratory arrest.

During a typical intubation procedure, a single trained paramedic, a physician, a Pre-Hospital Registered Nurse (PHRN), or any healthcare provider performs the intubation without assistance from other medical personnel. The intubation is generally accomplished by the healthcare provider who is performing the intubation procedure (referred to as the "intubater") holding a laryngoscope blade in one hand, placing the laryngoscope in the posterior of the pharynx of the patient, lifting the mandible upward and forward with a force sufficient to expose the glottic opening, and maintaining the view of the glottic opening for a period of time sufficient to permit the insertion of an endotracheal tube with the other hand.

This last step is the one that often causes the intubater significant problems. To lift the mandible for the exposure of the glottic opening, the intubater's left elbow is held out perpendicularly to the left lateral chest area. In this position, the intubater utilizes the small medial deltoid and posterior deltoid muscles to affect and maintain the desired position for intubation. If the intubater is slight of build or has an injury to the shoulder complex, he or she will have difficulty in the actual lift, or once attained, he or she will experience muscle exhaustion, fatigue or some degree of discomfort that could prevent the successful completion of the procedure.

When the intubater encounters an obstructed airway, secondary to a physical obstruction, that must be expeditiously removed, the muscle fatigue associated with the procedure is exacerbated. Under these circumstances, the patient's airway must be visualized for a much longer period of time, Magill forceps are utilized in conjunction with the laryngoscope blade, and the intubater's left hand and arm must suspend the mandible in an uplifted position during the entire procedure.

Since the patients requiring intubation are often in acute distress and in need of emergency care, the success of the intubation and the ability of the intubater to perform successful intubation quickly are critically important. According to a study conducted at Ohio state, the failure rate of intubation is about 29%. In most cases, intubation failure is associated with the intubater's inability to expose or maintain the visualization and subsequent exposure of the glottic opening that is necessary for successful insertion of the endotracheal tube into the tracheal area. The failure of an intubation may lead to a patient's death.

A need, therefore, exists for a device and method for providing mechanical assistance to allow an intubater some additional leverage that is necessary to accomplish intubation successfully without undue delay. The present invention meets this need. In addition, the present invention may be used to facilitate other oral cavity procedures. Furthermore, the present invention may be used during a surgical procedure, including, but not limited to, oral surgery, cephalic surgery, ocular surgery, and otolaryngologic surgery.

BRIEF DESCRIPTION OF THE FIGURES

For the purpose of illustrating the invention, the drawings show a form of the invention, which is presently preferred. However, it should be understood that this invention is not limited to the precise arrangements and instrumentalities shown in the drawings.

DETAILED DESCRIPTION OF THE INVENTION

Figure 1A:
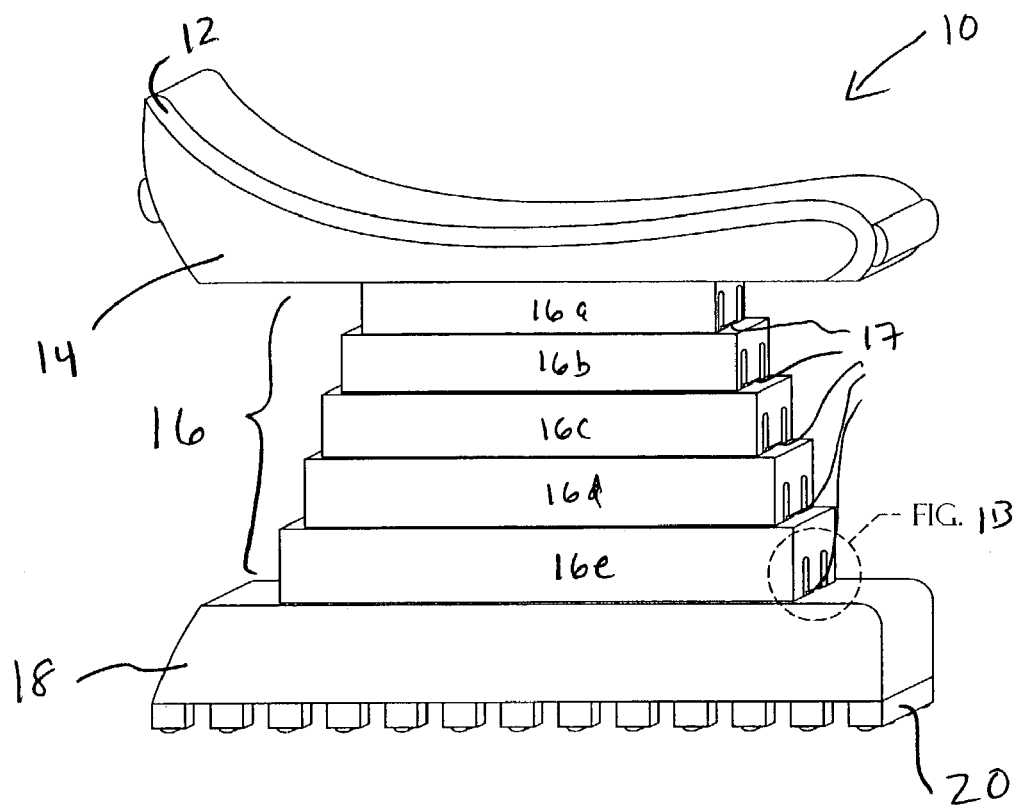
FIG. 1 is a schematic perspective view of a device in which the height adjuster comprises a plurality of telescoping sections, in accordance with an embodiment of the invention.

While the invention will be described in connection with one or more preferred embodiments, it will be understood that it is not intended to limit the invention to those embodiments. On the contrary, it is intended that the invention cover all alternatives, modifications and equivalents as may be included within its spirit and scope as defined by the appended claims.

Certain terminology is used herein for convenience only and is not to be taken as a limitation on the invention. Particularly, words such as "upper," "lower," "left," "right," "horizontal," "vertical," "upward," and "downward" merely describe the configuration shown in the figures. Indeed, the components may be oriented in any direction and the terminology, therefore, should be understood as encompassing such variations unless specified otherwise.

Referring now to the drawings, wherein like reference numerals illustrate corresponding or similar elements throughout the several views, the present invention is illustrated in various embodiments that are currently contemplated. Those skilled in the art would readily be capable of modifying these embodiments to practice the invention in alternate ways within the scope of the claims.

The mechanical device as disclosed in the present invention is adapted for use to provide an additional leverage for a healthcare provider to accomplish intubation successfully without undue delay. Also within the scope of the present invention, the mechanical device is for use by a healthcare provider when performing an endoscopy or a surgery.

Figure 1B:
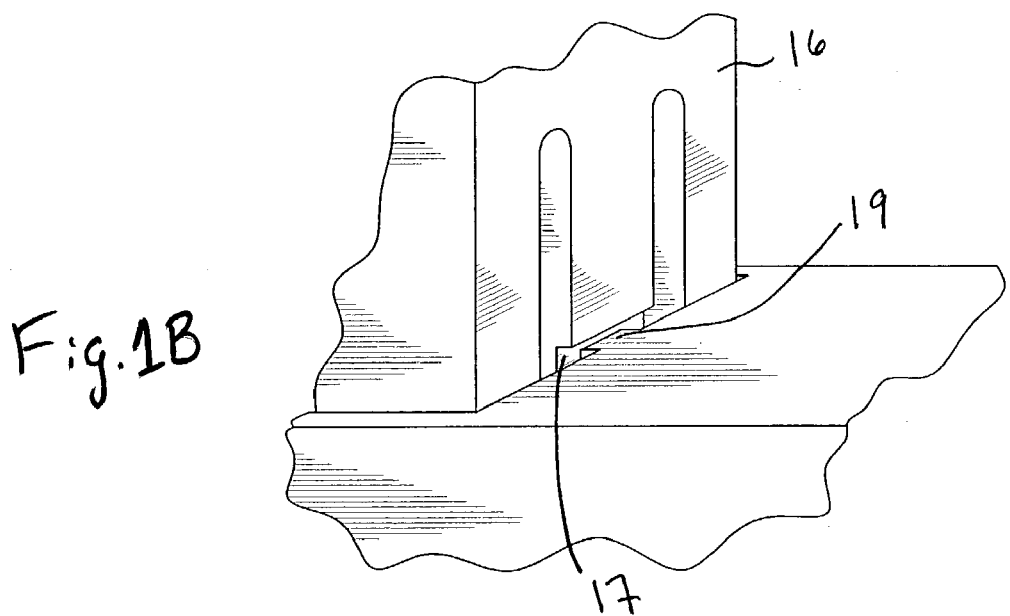
Figure 2:
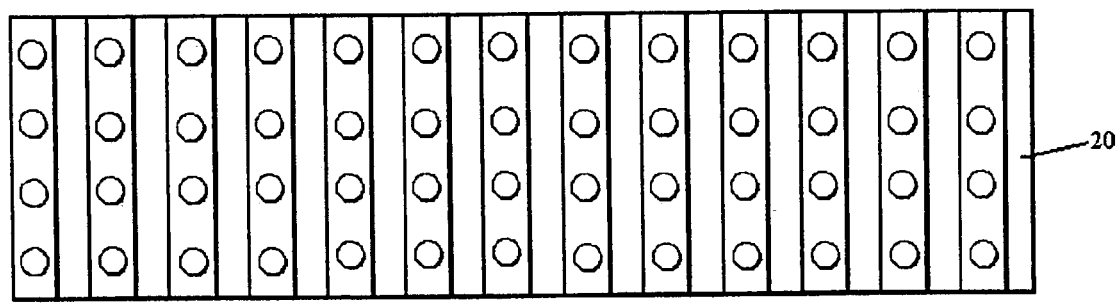
FIG. 2 is a schematic perspective view of the non-slip bottom surface when viewed from the bottom.

Referring now to FIG. 1, the device 10 of the present invention includes an elbow supporting platform 14, a height adjuster 16, and a base platform 18, wherein the height adjuster 16 is connected to and situated between the elbow supporting platform 14 and the base platform 18. The device may further include an elbow contacting element 12 that is connected to the elbow supporting platform 14. According to one embodiment of the present invention, the elbow contacting element 12 is tapered or indented toward its center for receiving a user's elbow and/or is cushioned. According to another embodiment, the elbow contacting element 12 is removable and replaceable from the supporting platform 14. Furthermore, the base platform 18 may comprise a non-slip bottom surface 20, such as a grooved bottom surface as shown in FIG. 2.

Figure 3:
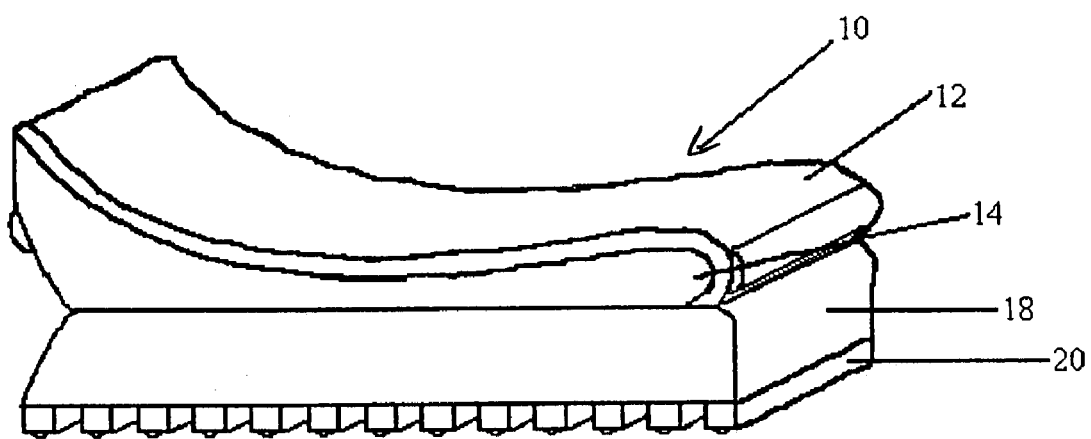
FIG. 3 is a schematic perspective view of the device of FIG. 1, wherein the device is in its collapsed position according to an embodiment of the invention.

The device has a height extending from the bottom of the base platform 18 to the top of the elbow supporting platform 14. In an exemplary embodiment, the height adjuster 16 can lock the device 10 at any one of a variety of heights ranging between 2–8 inches. FIG. 1A illustrates the device 10 in an expanded position and FIG. 3 illustrates a collapsed view of the device 10.

In the exemplary embodiment of the present invention shown in FIG. 1, the height adjuster 16 comprises a plurality of telescoping sections 16a–e. Each telescoping section 16a–d is received by another telescoping section 16b–e that is below it. Each telescoping section 16a–e may have a pair of indents 17 as shown in FIG. 1 or other means to lock the device at a desirable height. Each indent 17 is secured by a corresponding tab 19 on the telescoping section below it (or on the base platform 18 in the case of the bottom telescoping section 16e). The indents may be pushed inward and out of engagement with the tabs for returning the device 10 to a compressed position as shown in FIG. 3.

Figure 4:
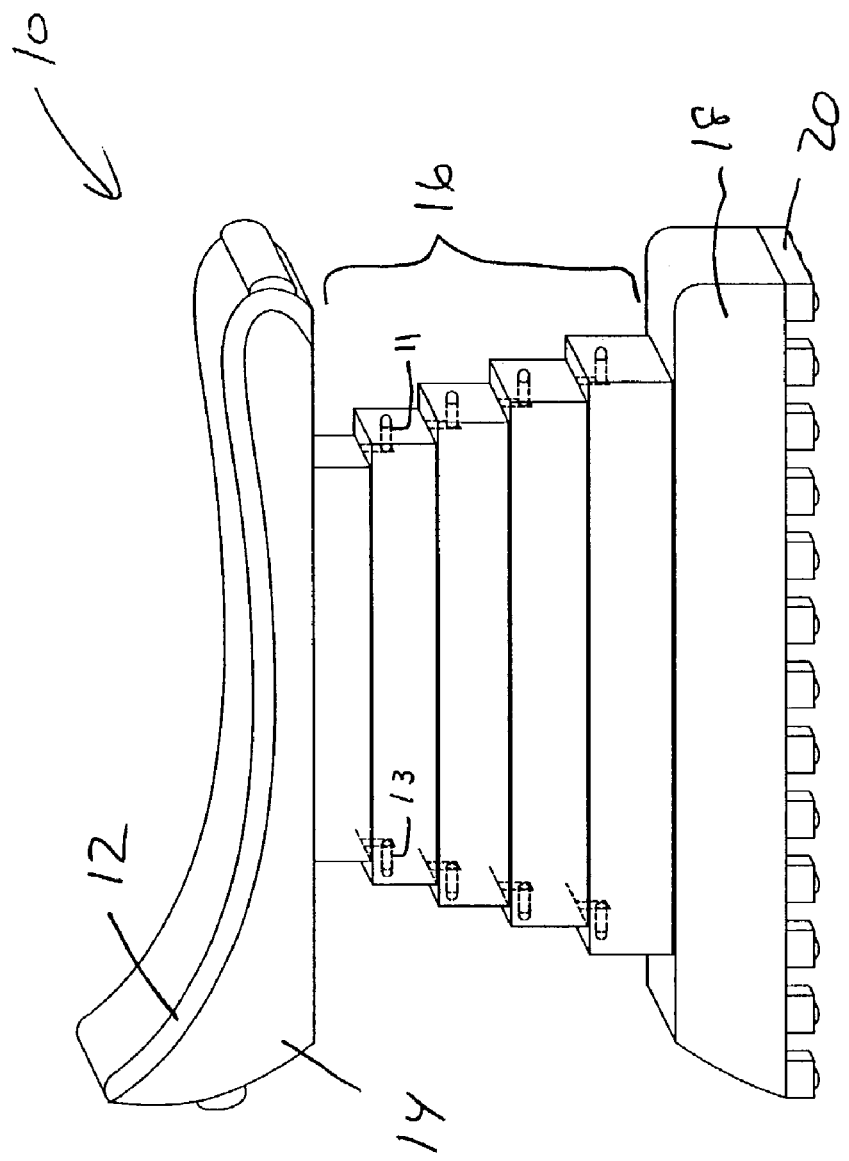
FIG. 4 is a schematic perspective view of a device in which the height adjuster comprises a plurality of telescoping sections, in accordance with an embodiment of the invention.

Another exemplary means of locking the device at a desirable height is illustrated in FIG. 4. Each telescoping section 16a–e includes one or more pins 13 that protrude through corresponding apertures 11 in the telescoping section below it when it is extended from a compressed position. The pins 13 may be inserted into the apertures 11 while compressing the device 10 to return the device to a compressed position as shown in FIG. 3.

Figure 5:
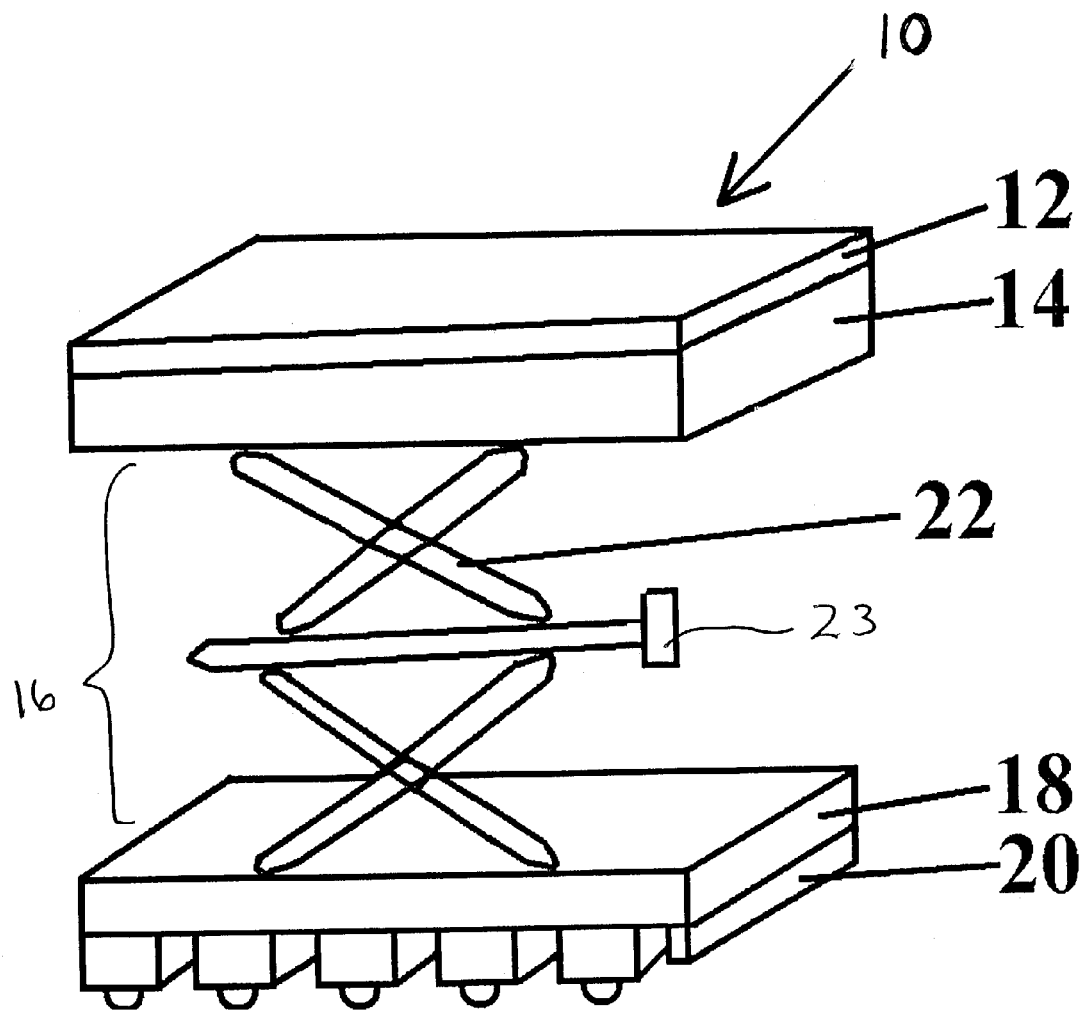
FIG. 5 is a schematic perspective view of a device in which the height adjuster is incorporated as a scissors lift, in accordance with an embodiment of the invention.

In the exemplary device 10 as illustrated in FIG. 5, the height adjuster 16 comprises a scissors lift 22 and a means to lock the scissors lift 22 at a variety of heights. The scissors lift 22 may be raised, lowered, and locked by a threaded screw 23 as illustrated in FIG. 5. The threaded screw 23 may be rotated in one direction to raise the elbow supporting platform 14, rotated in an opposite direction to lower the elbow supporting platform 14, and fixed in position (i.e., not rotated) to lock the scissors lift 22.

Figure 6:
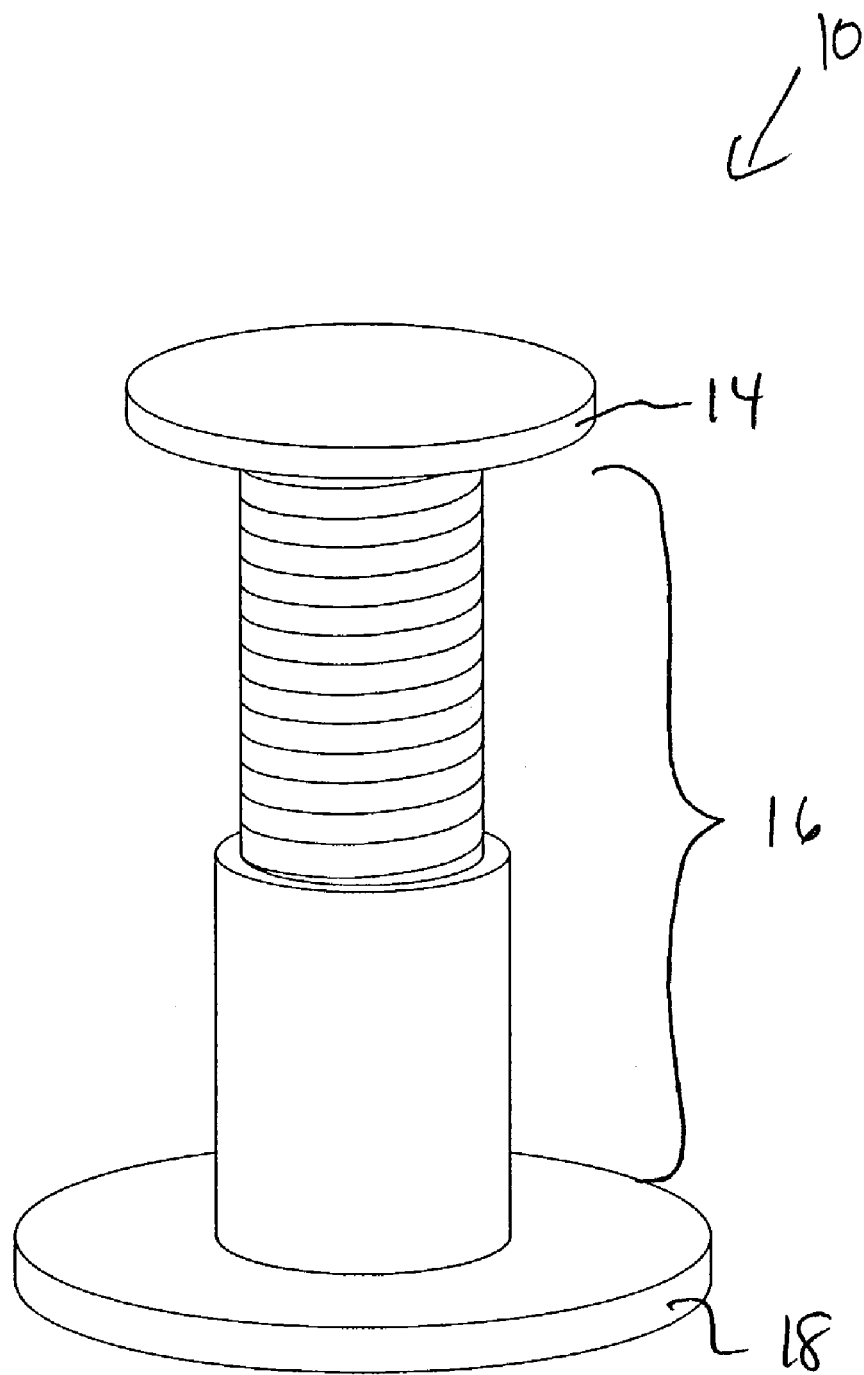
FIG. 6 is a schematic perspective view of a device in which the height adjuster comprises a threaded coupling, in accordance with an embodiment of the invention.

In the exemplary device 10 shown in FIG. 6, the height adjuster 16 comprises a threaded coupling between the elbow supporting platform 14 and the base platform 18. The elbow supporting platform 14 and the base platform 18 may be rotated in one direction to increase the device height and rotated in the opposite direction to decrease the device height.

The present invention provides a hospital version of the device. As the hospital version device will be used on a hospital bed or an operating table, it is preferred that the device have a wide base platform to allow for downward displacement into a cushioned mattress. One example of the hospital version device has a base platform of about 6×8 inches. Also provided is a portable street version of the device that is used by a paramedic or a PHRN. The street version of the device may have a collapsed size that is small enough to fit into the pocket of the paramedic or PHRN. One example of the portable street version device may have a base platform of about 4×6 inches, and a collapsed height of about 2 inches.

Figure 7:
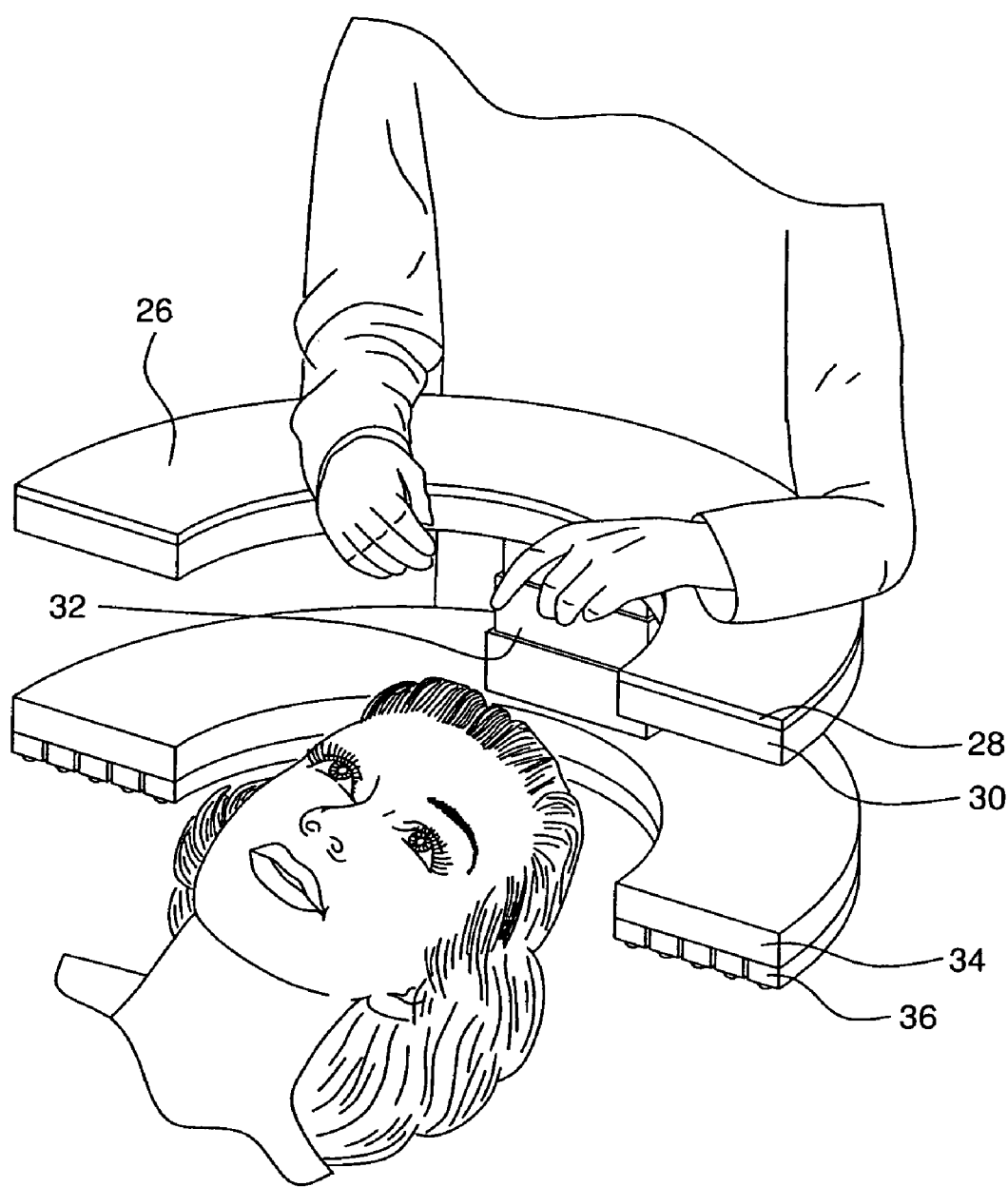
FIG. 7 is a schematic perspective view of a device in which the elbow supporting platform has a "U" shape, in accordance with an embodiment of the invention.

In the exemplary embodiment of the present invention illustrated in FIG. 7, the elbow supporting platform 30 of the device 26 has a "U" shape when viewed from the top of the elbow supporting platform 30. A height adjuster 32 is connected to and situated between the elbow supporting platform 30 and a base platform 34. An elbow contacting element 28 is connected to the elbow supporting platform 30. The device 26 is sized to allow a healthcare provider place both of his/her elbows upon the elbow contacting element 28. This embodiment may provide mechanical leverages to both elbows of the healthcare provider.

The present invention also provides a method of using the device by an intubater, i.e., a healthcare provider, including but not limited to, a physician, a PHRN or a paramedic. During the intubation procedure, the intubater may position the device at a desirable height, resting one or both elbows on one or more devices for the leverage necessary to expose, and maintain the exposure of, the patient's glottic opening.

The present invention further provides a method of using the device by a healthcare provider when performing a medical procedure, including but not limited to, endoscopy, an oral surgery, a cephalic surgery, an ocular surgery, and an otolaryngologic surgery. During the medical procedure, the healthcare provider may rest one of his or her elbows on the device for support. It is also within the scope of the present invention that the healthcare provider rests both of his or her elbows on the device 26 with a "U" shaped elbow supporting platform 30, as illustrated in FIG. 7.

Figure 8:
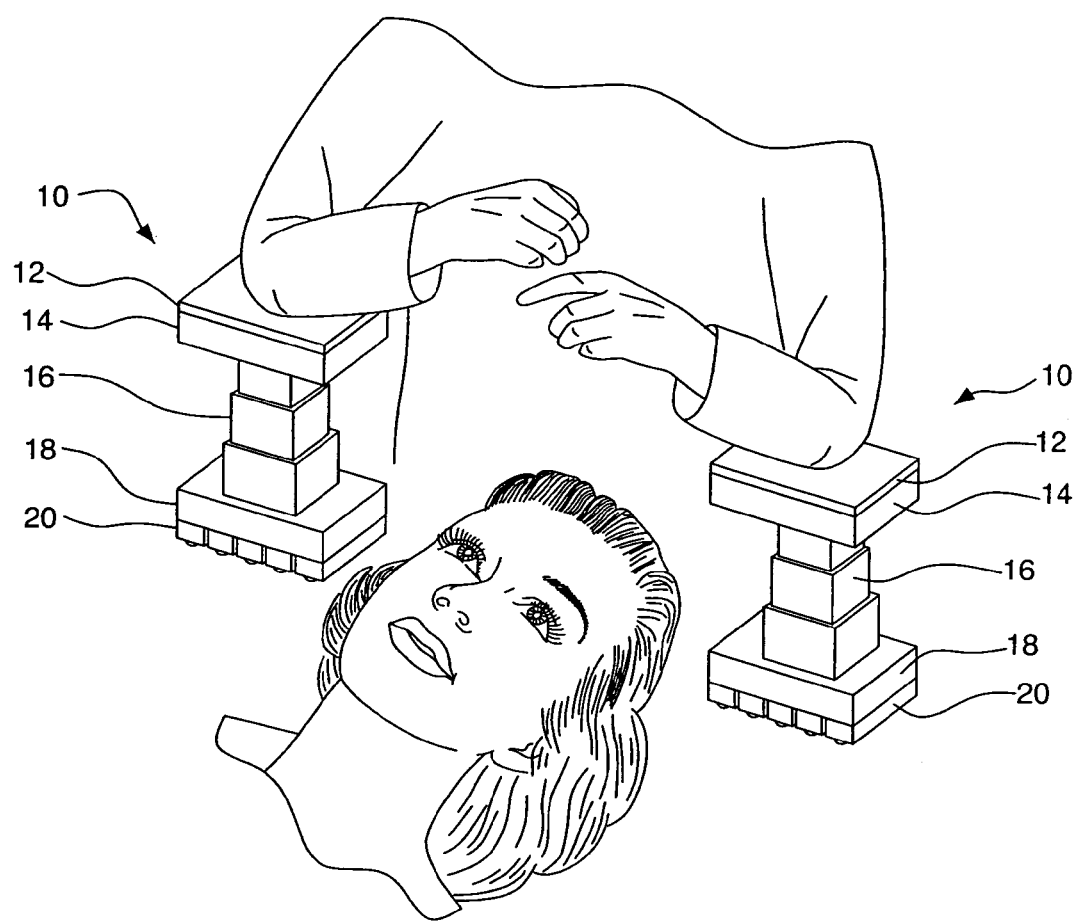
FIG. 8 is a schematic perspective view of two devices of FIG. 1, wherein the two devices are used by a healthcare provider when performing a surgery on a patient, in accordance with an embodiment of the invention.

According to another method of the present invention, a healthcare provider may uses two devices 10 for performing an oral cavity or cephalic region procedure as illustrated in FIG. 8. The a healthcare provider may to rest each elbow on a separate device during the procedure as shown in FIG. 8.

In an exemplary embodiment, the device 10 is made of non-infective non-porous material that can be sterilized after each use. Possible materials include, but are not limited to, stainless steel or plastic.

As used herein, the term "oral cavity" comprises the glottic opening, the pharynx, and the nasopharynx. The device according to the present invention may be used while perform various procedures including, but not limited to, one or more of the group of an endoscopy, an intubation, oral surgery, cephalic surgery, ocular surgery, and otolaryngologic surgery. Although use of the invention is described above with regard to procedures performed on humans, the invention may be used on many other species, including but not limited to, mammalian, bovine, ovine, porcine, equine, rodent and human.

While this invention has been described with a reference to specific embodiments, it will be obvious to those of ordinary skill in the art that variations in these methods and compositions may be used and that it is intended that the invention may be practiced otherwise than as specifically described herein. Accordingly, this invention includes all modifications encompassed within the spirit and scope of the invention as defined by the claims.

What is claimed is:

1. A device for providing a mechanical leverage to at least one elbow of a healthcare provider when said healthcare provider is performing an intubation or a surgery on a patient, comprising: an elbow supporting platform, a height adjuster and a base platform, wherein
    said height adjuster is connected to said elbow supporting platform and said base platform; and
    said height adjuster is situated between said elbow supporting platform and said base platform,
    said height adjustor adapted to expand and collapse to respectively raise and lower said elbow supporting platform with respect to said base platform.

2. A device for supporting at least one elbow of a healthcare provider for providing mechanical leverage to the healthcare provider while performing an oral cavity or cephalic region procedure on a patient, the device comprising:
    an elbow supporting platform;
    a base platform; and
    a height adjuster connected to the elbow supporting platform and to the base platform and securing the elbow supporting platform in spaced relation to the base platform,
    said height adjustor adapted to expand and collapse to respectively raise and lower said elbow supporting platform with respect to said base platform.

3. The device of claim 2, further comprising an elbow contacting element, wherein said elbow contacting element is connected to a top surface of said elbow supporting platform.

4. The device of claim 3, wherein said elbow contacting element is cushioned.

5. The device of claim 3, wherein said elbow contacting element is removably connected to said elbow supporting platform.

6. The device of claim 2, wherein said height adjuster can adjustably secure the elbow supporting platform in spaced relation to and at any of a plurality of distances from the base platform.

7. A device for supporting at least one elbow of a healthcare provider for providing mechanical leverage to the healthcare provider while performing an oral cavity or cephalic region procedure on a patient, the device comprising:
    an elbow supporting platform;
    a base platform; and
    a height adjuster connected to the elbow supporting platform and to the base platform and securing the elbow supporting platform in spaced relation to the base platform, wherein said height adjuster can adjustably secure the elbow supporting platform in spaced relation to and at any of a plurality of distances from the base platform, and
    wherein said height adjuster comprises a plurality of telescoping sections.

8. The device of claim 6, wherein said height adjustor is a scissors lift.

9. The device of claim 6, wherein the device has a height from a bottom of the base platform to a top surface of the elbow supporting platform and the plurality of distances correspond to device heights ranging from about 2–8 inches.

10. The device of claim 2, wherein said device has a length of about 8 inches and a width of about 6 inches.

11. The device 2, wherein said device has a length of about 6 inches, a width of about 4 inches, and a collapsed height of about 2 inches.

12. The device of claim 2, wherein said base platform further comprises a non-slip bottom surface.

13. A device for supporting at least one elbow of a healthcare provider for providing mechanical leverage to the healthcare provider while performing an oral cavity or cephalic region procedure on a patient, the device comprising:
    an elbow supporting platform;
    a base platform; and
    a height adjuster connected to the elbow supporting platform and to the base platform and securing the elbow supporting platform in spaced relation to the base platform, wherein said base platform further comprises a non-slip bottom surface, and
    wherein said bottom surface is grooved.

14. The device of claim 2, wherein said device is made of non-infective material.

15. The device of claim 2, wherein said elbow supporting platform has a "U" shape when viewed from top of said elbow supporting platform.

16. A method for performing intubation or surgery on a patient comprising the steps of resting at least one elbow on a device according to claim 2 for providing mechanical leverage and performing the intubation or surgery on the patient.

17. The method according to claim 16 further comprising the step of expanding the device from a compressed position to an expanded position.

18. A method for performing intubation or surgery on a patient comprising the steps of securing the elbow supporting platform of a device according to claim 5 in spaced relation to the base platform, resting at least one elbow on the device, and performing the intubation or surgery on the patient.

* * * * *